US011932875B2

(12) United States Patent
Livingston et al.

(10) Patent No.: US 11,932,875 B2
(45) Date of Patent: Mar. 19, 2024

(54) METHODS AND DEVICES FOR CONTROLLING STEM CELL FUNCTION AND GENE EXPRESSION

(71) Applicant: The Aerospace Corporation, El Segundo, CA (US)

(72) Inventors: Frank Edward Livingston, Redondo Beach, CA (US); Timothy Ganey, Tampa, FL (US)

(73) Assignee: THE AEROSPACE CORPORATION, El Segundo, CA (US)

( * ) Notice: Subject to any disclaimer, the term of this patent is extended or adjusted under 35 U.S.C. 154(b) by 599 days.

(21) Appl. No.: 16/869,208

(22) Filed: May 7, 2020

(65) Prior Publication Data
US 2021/0348130 A1 Nov. 11, 2021

(51) Int. Cl.
C12N 5/0775 (2010.01)
B23K 26/0622 (2014.01)

(52) U.S. Cl.
CPC ........ C12N 5/0662 (2013.01); B23K 26/0622 (2015.10); C12N 2529/10 (2013.01); C12N 2533/90 (2013.01)

(58) Field of Classification Search
None
See application file for complete search history.

(56) References Cited

U.S. PATENT DOCUMENTS

| 8,679,189 B1 | 3/2014 | Ganey et al. |
| 10,228,666 B2 | 3/2019 | Livingston et al. |

OTHER PUBLICATIONS

Cunha et al. "Human mesenchymal stem cell behavior on femtosecond laser-textured TI-6AI-4V surfaces" (2015), Nanomedicine 10(5): 725-739. (Year: 2015).*
Livingston et al. "Genotype-inspired laser material processing: a new experimental approach and potential application to protean materials." (2008), Appied Physics A 93(1): 75-83 (Year: 2008).*
Gittard & Narayan "Laser direct writing of micro- and nano-scale medical devices" (2010), Expert Reviews, vol. 7(3): 343-356. (Year : 2010).*
Davies et al., "Stemistry: The Control of Stem Cells in Situ Using Chemistry", J. Medicinal Chem., Jan. 15, 2015, pp. 2863-2894, (5), American Chemical Society, Washington, DC.
James et al., "A Review of the Clinical Side Effects of Bone Morphogenetic Protein-2", Tissue Engineer. Part B Rev., Apr. 13, 2016, pp. 284-297, vol. 22 Issue 4, Mary Ann Liebert, Inc., Larchmont, NY.
Li et al., "Concise Review: A Chemical Approach to Control Cell Fate and Function", Stem Cells, Jan. 2012, pp. 61-68, vol. 30, Issue 1, John Wiley & Sons, Inc., Hoboken, NJ.
Livingston et al., "Multi-Layer Substrate Apparatus, Systems and Methods of Assembling Same", U.S. Appl. No. 16/212,638, filed Dec. 6, 2018, 12 pages.
Mashinchian et al., "Regulation of stem cell fate by nanomaterial substrates" Nanomedicine, Mar. 30, 2015, pp. 829-847, vol. 10, No. 5, Future Medicine Ltd, London, United Kingdom.
Von Der Mark et al., "Nanoscale engineering of biomimetic surfaces: cues from the extracellular matrix", Cell Tissue Res., Jan. 2010, pp. 131-153, 339, Springer Nature, Basingstoke, United Kingdom.

* cited by examiner

Primary Examiner — Teresa E Knight
(74) Attorney, Agent, or Firm — Morgan, Lewis & Bockius LLP

(57) ABSTRACT

A method of stimulating and controlling stem cell activity and differentiation on a modified material substrate and a device including the modified material substrate are provided. The method includes providing a material substrate configured for medical use. The material substrate includes at least one surface or interior area available for modification, and the at least one surface or interior area is treated with a plurality of pulsed light beams to obtain a modified material substrate with at least one modified surface or interior area. The at least one modified surface or interior area has a biomimetic architecture with surface and bulk (interior) features, properties, and textures configured to accelerate and control stem cell differentiation when the modified material substrate is contacted with stem cells.

14 Claims, 10 Drawing Sheets

Implant

Bio-Network

3-D Scaffold

2-D Template

Laser-processed PEEK

Laser-processed PEEK

METHODS AND DEVICES FOR CONTROLLING STEM CELL FUNCTION AND GENE EXPRESSION

FIELD

The disclosure relates generally to a method and device for controlling stem cell differentiation and gene expression, and more particularly, to a method for controlling stem cell differentiation and gene expression on a substrate modified by a plurality of pulsed light beams.

BACKGROUND

Stem cells are cells that can differentiate into other types of cells. The fate of a stem cell is dictated by its in vivo or in vitro microenvironment ("niche"). Each type of stem cell (embryonic, adult, stromal, and induced pluripotent) exists in a niche that is exclusive to that cell type and offers a unique set of biological instructions that define the function of that stem cell. A native niche comprises extracellular matrix (ECM) constituents and other biomolecular components that transfer biologic and genetic instructions through chemical, physical, and topographical pathways (the three principal cues or "triad" for cell signaling). Chemical cues include growth hormones, proteins (cytokines and chemokines), and other metabolic molecules that bind to cell membrane receptors to support cell proliferation and differentiation. Physical cues include mechanical stimuli, such as compression, fluid shear and stress, and regulate cell organization and tissue architecture by activating mechanosensitive ion channels and protein kinases, which can lead to the expression of specific lineages and genes in stem cells. Surface topography and textures can influence cell shape, cell attachment, and cell motility, controlling focal adhesion kinetics, and directing stem cell multipotency and differentiation.

Approaches for activating and controlling stem cells include chemical, physical, and topographic analogs that mimic the native niche, seeking to achieve the triad required for effective cell signaling and cell communication. A variety of small molecules, including artificial growth factors (signaling polypeptides) and synthetic biomolecules, have been designed and implemented to regulate cell activity and function, and to drive stem cell proliferation and differentiation. These approaches have received attention in the areas of musculoskeletal tissue repair and tissue regeneration. Recombinant human bone morphogenetic proteins or rhBMPs, for example, have been used to treat a number of bone disorders and skeletal injuries, including long bone fractures, spinal fusions, and oral surgery.

Existing stem cell therapies and activation methods have significant health risks and biological limitations that present formidable challenges to their universal adoption and safe long-term application. A major concern associated with small-molecule therapeutics corresponds to their dose requirements and non-specific side effects. For example, extremely large rhBMP doses are needed to achieve clinical effectiveness, exceeding natural hormonal levels by a factor of more than one million. The excessive dosages have been shown to cause serious inflammatory reactions, ectopic bone formation, and increased rates of benign neoplasia. Due to their size, small molecules are also prone to enter non-target cells and elicit unwanted physiological responses. Regulatory burdens and manufacture cost are increased appreciably by the incorporation of biomolecular adjuncts and growth factors into medical devices and therapies.

Material substrates, such as skeletal implant structures and related interbody devices, can be used for various applications ranging from surgical repairs and orthopedic restoration to regenerative medicine and pain mitigation therapies. Some material substrates, such as implants, include passive structural systems whose physical and chemical properties are intended to align with, for example, human bone, to enable mechanical integrity and biocompatibility for long-term acceptance into the skeletal structure. One of ordinary skill in the art would appreciate that some known approaches are used to facilitate integration of the material substrate, such as the implant, into a body. For example, mechanical manipulation and chemical treatments can be used to affect surface structure and roughness prior to implantation. Electrochemical stimuli can be used to govern cellular activity and function in the human body, stimulating cell activity at the implant site and improving interbody integration. Other techniques, such as the use of direct current, inductive coupling, capacitive coupling, and low-intensity pulsed ultrasound, can also be used to facilitate integration of the material substrate into the body.

In spite of these techniques, many material substrates, such as implants, require external intervention and therapeutic options before enhancing, for example, tissue growth and bone fusion, for improving fixation and stability. However, the restorative devices and methods can be invasive and, in some circumstances, require additional surgery, bulky power sources, and/or frequent maintenance. The lack of customization and genetic design, along with patient non-compliance, can further amplify the challenges associated with current implant approaches.

SUMMARY

In various embodiments, a method of stimulating and controlling stem cell differentiation on a modified material substrate is disclosed. The method comprises providing a material substrate configured for medical use, wherein the material substrate comprises at least one surface or interior (bulk) location available for modification, and treating the at least one surface or interior location with a plurality of pulsed light beams to obtain a modified material substrate comprising at least one modified surface or interior location, the at least one modified surface or interior bulk material comprising a biomimetic architecture comprising surface and bulk features, properties, and textures configured to accelerate and control stem cell differentiation when the modified material substrate is contacted with stem cells.

In various embodiments, a device configured for medical use is provided. In some embodiments, the device comprises a modified material substrate comprising at least one modified surface or interior (bulk) location comprising a biomimetic architecture comprising surface and bulk features, properties, and textures configured to accelerate and control stem cell differentiation when the modified material substrate is contacted with stem cells, wherein the biomimetic architecture of the modified material substrate was obtained by treating a corresponding at least one surface or interior location of a corresponding material substrate with a plurality of pulsed light beams.

Additional features and advantages will be set forth in the detailed description which follows, and in part will be apparent to those skilled in the art from that description or recognized by practicing the embodiments described herein, including the detailed description which follows, the claims, as well as the appended drawings.

It is to be understood that both the foregoing general description and the following detailed description describe various embodiments and are intended to provide an overview or framework for understanding the nature and character of the claimed subject matter. The accompanying drawings are included to provide a further understanding of the various embodiments and are incorporated into and constitute a part of this specification. The drawings illustrate the various embodiments described herein and, together with the description, explain the principles and operations of the claimed subject matter.

DETAILED DESCRIPTION

Figure 1:
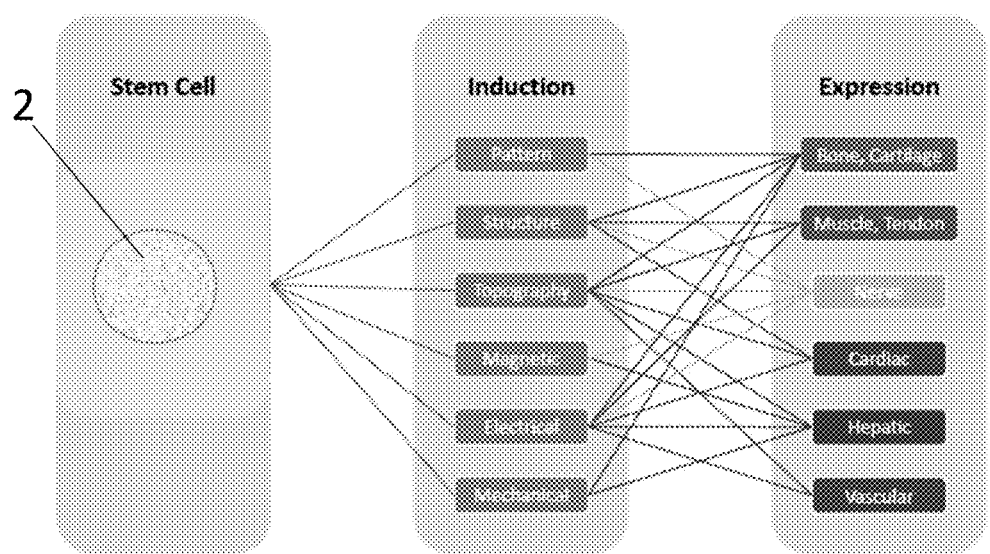
FIG. 1 is block diagram showing the connectivity between the laser-scripted inductions and the related gene expressions in stem cells, in accordance with some embodiments of the present disclosure.

Reference will now be made in detail to embodiments of the present disclosure, examples of which are illustrated in the accompanying drawings. Whenever possible, the same reference numerals will be used throughout the drawings to refer to the same or like parts. However, this disclosure may be embodied in many different forms and should not be construed as limited to the embodiments set forth herein.

In various embodiments, a method of controlling stem cell differentiation and gene expression is disclosed. As shown in FIG. 1, one or more inductions (for example, pattern, structure, topography, magnetic, electrical, mechanical) can induce a stem cell (2) to differentiate into a particular cell type having a specific gene expression and cell function. As shown in FIG. 2, in some embodiments, the method comprises providing a material substrate (4), modifying the material substrate (4) with an energy source (6) (not shown) to obtain a modified material substrate (8), and exposing a stem cell to the modified material substrate (8) to transform the stem cell into a cell having a desired gene expression and cell function (for example, bone cell, nerve cell, vascular cell, etc.).

The method is not limited to any particular material substrate (4); i.e., the method can be applied to any material class or device. In some embodiments, the material substrate (4) comprises commonly employed biomaterials, such as biocompatible organic thermoplastics, glass, ceramics, metals (for example, titanium) and metal alloys (for example, stainless steel), bone, allografts, semiconductors, dielectrics, or any combination thereof. In such embodiments, and without limitation, the material substrate (4) can be a biocompatible and/or implantable-grade material, such as a polyether ether ketone (PEEK), polyetherketoneketone (PEKK), polyethylene, ultra-high molecular weight polyethylene, polyphenylsulfone, polysulfone, polythermide, acetal copolymer, lennite UHME-PE, human allografts (cortical bone), bioceramics, tissue, glass, or any other suitable biocompatible and/or implantable-grade material.

The energy source (6) can be any suitable source of pulsed light beams. In some embodiments, the energy source (6) is a laser configured to generate a plurality of pulsed light beams. In some embodiments, other types of energy sources can be used, such as electron beams, x-rays, proton beams, and lamp and arc sources.

Lasers or other light sources have the unique property of delivering precise photonic energy at a distance. As a consequence, laser processing can be physically non-intrusive and conducted on a local scale. Laser processing techniques are applicable to many different types of materials, such as metals, glass, ceramics, polymers, semiconductors, bioceramics, bone, and tissue, with a scale resolution that can approach the wavelength of light. Laser processing techniques offer excellent precision and control. As a result, laser processes can be used to remove material with very high precision, aid in the deposition of materials, alter the phase of processed materials, or act as a spectroscopic monitor during processing.

In various embodiments, the energy source (6) comprises a laser pulse script. A laser pulse script can be generated for laser machining, whereby a sequence of concatenated laser writing processes defines the laser pulse script for performing a sequence of laser writing processes or machining functions. Prior to laser writing, sample measurements can be conducted on various materials and surfaces to determine the optimum laser parameters. These parameters may be the photonic dose in photons per unit area, intensity in power per unit area, fluence in energy per unit area, as well as a pulse repetition rate, for the machining the sample to possess the desired photophysical and photochemical properties. These measurements are performed on individual material samples. The results of the measurements can then be recorded for later use on various samples having a material determined by the measurement. The results of these measurements comprise a genotype pulse script sequence that is a set of information and instructions that describe how to achieve a desired photophysical and photochemical property.

Systems for generating laser genotype pulse scripts are described in U.S. Pat. No. 7,526,357, entitled PULSE MODULATION LASER WRITING SYSTEM, issued on Apr. 28, 2009; U.S. Pat. No. 8,679,189, entitled BONE GROWTH ENHANCING IMPLANT, issued on Mar. 25, 2014; U.S. Pat. No. 10,228,666, entitled MATERIAL MODIFICATION ASSEMBLY AND METHOD FOR USE IN THE MODIFICATION OF MATERIAL SUBSTRATES, issued on Mar. 12, 2019; and co-pending U.S. patent application Ser. No. 15/469,132, entitled SYSTEMS AND METHODS FOR MODIFYING MATERIAL SUBSTRATES, filed Mar. 24, 2017; the contents of which incorporated herein by reference in their entireties.

In some embodiments, the method of controlling stem cell differentiation and gene expression utilizes laser genotype pulse scripts to encode instructions for stem cell communication and control. In such embodiments, the laser genotype pulse scripts can be tailored and designed to elicit a diverse array of material modifications and inductions on the material substrate. In some embodiments, the material modifications and inductions are singular and homogeneous. In some embodiments, the material modifications and inductions are multiplexed and heterogeneous. One of ordinary skill in the art would appreciate that the selection of the laser-tailored modifications and inductions can depend upon the physiological response and biological expression needed. In these embodiments, the method of controlling stem cell differentiation and gene expression comprises no chemical or pharmacological adjuncts to communicate instructions to the stem cells.

In some embodiments, the laser genotype pulse scripts result in biomimetic architectures that retain biological instruction capability through variable bio-geometry that is perceived in surface and bulk (volume) response, and through inductive and conductive pathways resulting from phase disposition and composition. In some embodiments, the surface interactions are manifested as micro-structural modifications, nano-topography alterations, and/or patterns with appropriate repetition and design to enhance biologic response and cell efficacy. In some embodiments, the laser-induced modifications also include charge distribution, electric field variation, standing voltaics, and capacitively-contained field charges to accentuate cell differentiation and tissue regeneration. In some embodiments, the laser-induced modifications include conductive, instructive, and inductive properties. In some embodiments, the laser-induced modifications are exercised as magneto-mechanical, electromechanical (ferroelectric, piezoelectric), and elementally enhanced inclusions to regulate cell chemistry and drive discrete phenotype expression.

In some embodiments, the laser-tailored modifications and inductions are spatially mapped to discrete physiological and biological processes, presenting new patient-specific treatment options in implant technology, orthopedics, tissue engineering, organ production, drug screening, etc. The method induces material alterations that are position-synchronized, spatially-coordinated, and defined through physics and energy-based transduction mechanisms. In such embodiments, the modified material substrate, having encoded information and genetic instructions in the form of the laser-tailored modifications (e.g., phase changes, structural changes, etc.), is adapted to communicate instructions to stem cells in order to induce the desired cell response, cell activity, and cell function. The instructions can govern stem cell attachment and cell proliferation on a material substrate, as well as the differentiation and phenotype of cells. According to such embodiments, gene expression and stem cell fate can be dictated, ultimately determining whether the stem cells transform into bone cells, nerve cells, vascular cells, etc.

In some embodiments, the laser genotype pulse scripts comprise discrete pulse sequences that can be modulated in amplitude (intensity), pulse duration (pulse width), frequency (repetition rate), polarization (electric-field orientation), and coherence, or any combination thereof, to encode instructions for stem cell communication and control. The laser genotype pulse scripts can result in a modified material substrate having variable forms and dispositions that range from patterned structural modifications to electrical, magnetic, and mechanical inductions. In some embodiments, the biologically active, physiologically-mapped architecture is an interconnected, multi-functional network.

In some embodiments, the laser genotype pulse scripts can be tailored and designed to elicit a diverse array of material modifications and inductions. In some embodiments, the material modifications and inductions are singular and homogeneous. In some embodiments, the material modifications and inductions are multiplexed and heterogeneous. One of ordinary skill in the art would appreciate that the selection of the laser-tailored modifications and inductions can depend upon the physiological response and biological expression needed.

Many factors are used in generating the laser genotype pulse scripts (6), including the laser wavelength. In some embodiments, for example, the laser pulses can be a sequence of multiple laser pulses, each at a different amplitude, or a continuously varying photon flux. As shown in FIGS. 2A-2D, for example, the native material substrate (4) can be modified with one or more laser genotype pulse scripts (for example, 6a-6d) to form a modified ("programmed") material substrate (8) having one or more modified surfaces (18) and a modified internal bulk (19). An enlarged view of the laser genotype pulse scripts (6a-6d) is provided in FIG. 2B. As shown in the figure, each of the laser genotype pulse scripts comprise discrete pulse sequences having variable differences in amplitude (intensity), pulse duration (pulse width), and frequency (repetition rate).

Figure 2A:
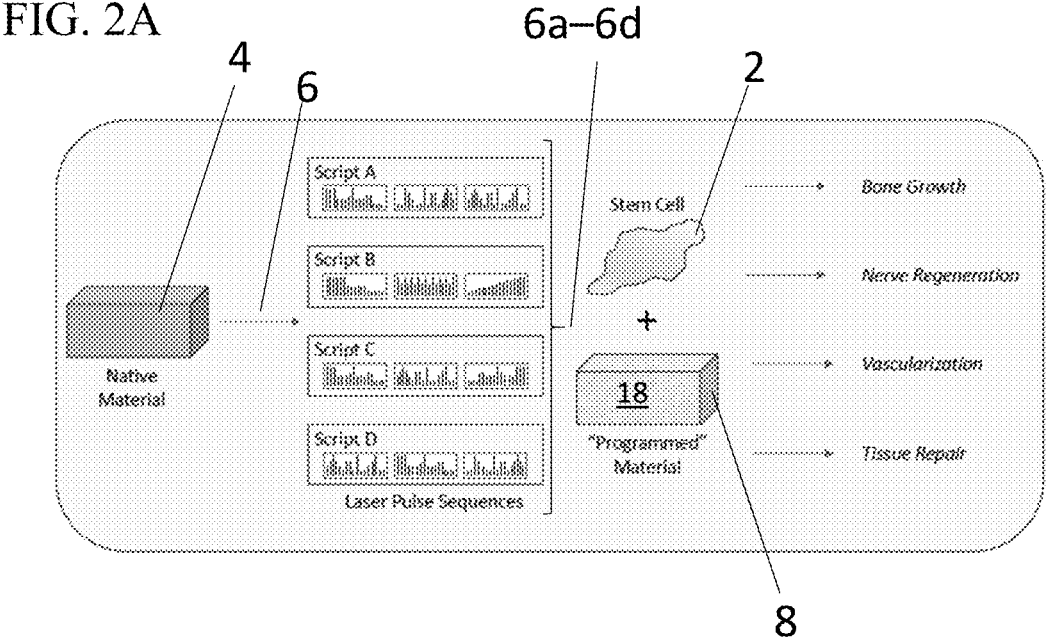
FIG. 2A is a block diagram of laser biomimetic processing utilizing discrete pulse sequences (laser genotype pulse scripts) to create interconnected material states on a material substrate, and encoding the material substrate with intelligent signatures to control stem cell fate and multi-lineage character, in accordance with some embodiments of the present disclosure.
Figure 2B:
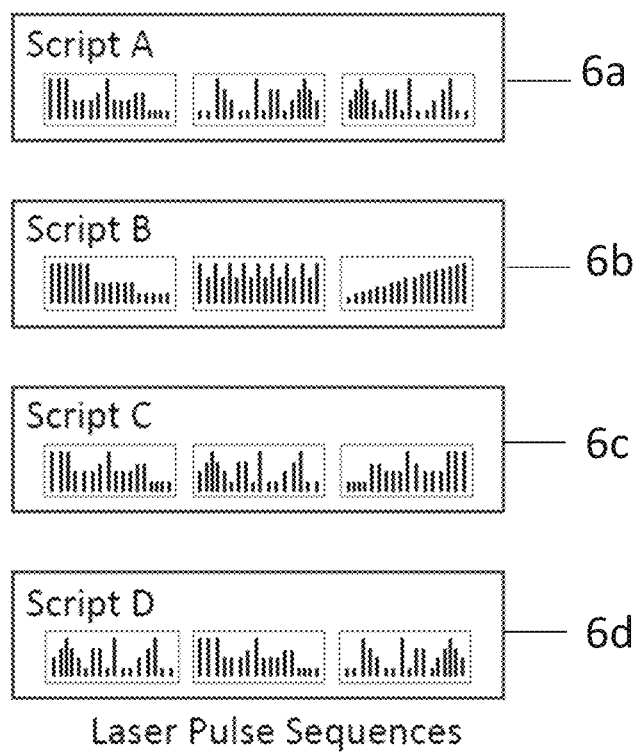
FIG. 2B is an enlarged view of the exemplary laser genotype pulse scripts (6a-6d) in FIG. 2A.
Figure 2C:
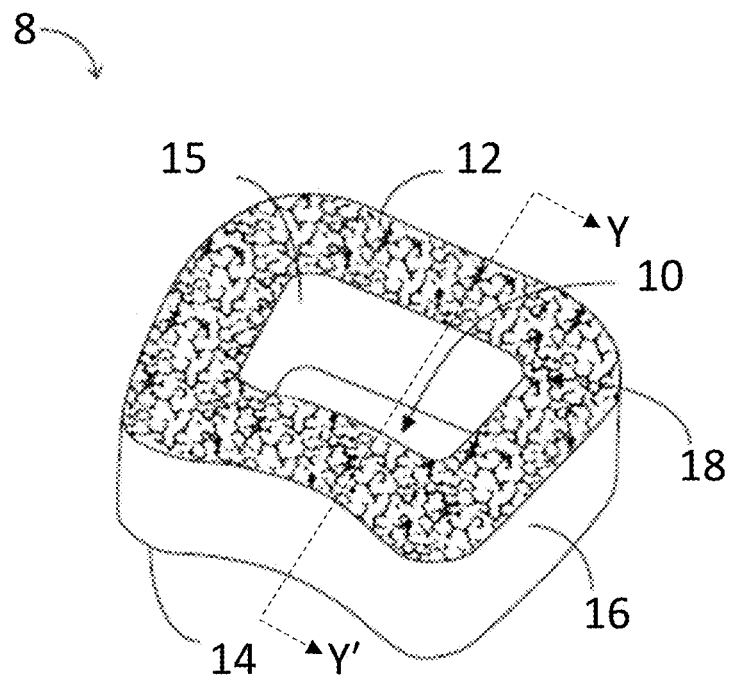
FIG. 2C is a perspective view of a modified material substrate (8)

In FIG. 2C, the modified material substrate (8) has a substantially cylindrical shape and a channel (10) defining an internal surface (15) therethrough, whereby the channel (10) extends through a top exterior surface (12) and a bottom exterior surface (14) of material substrate (8). A side exterior surface (16) substantially circumscribes at least a portion of material substrate (8) such that top exterior surface (12), bottom exterior surface (14), and channel (10) are not enclosed or covered by the side exterior surface (16).

Figure 2D:
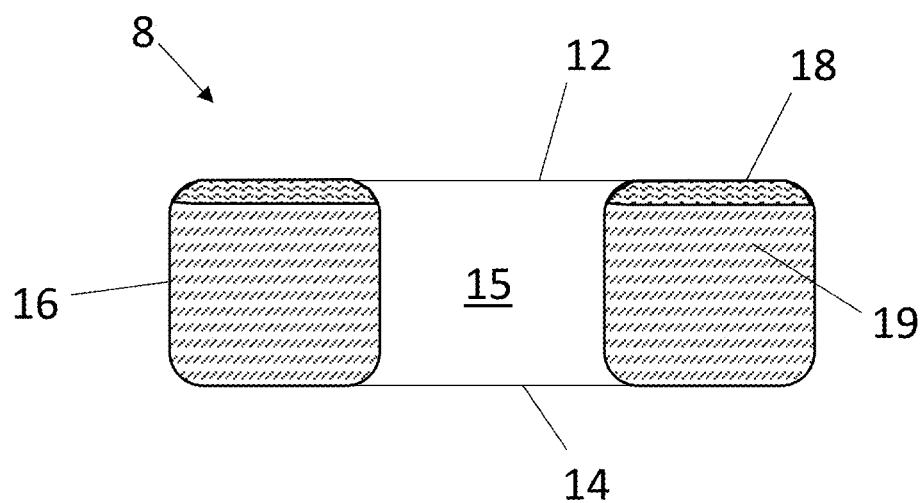
FIG. 2D is a cross-sectional view through the Y-Y' line of the modified material substrate (8) in FIG. 2C.

As shown in FIGS. 2C and 2D, the top surface (12) includes structural modifications. When the one or more modified surfaces (18) are exposed to stem cells (2), as shown in FIG. 2A, the laser genotype pulse scripts (6a-6d) encode instructions in the modified surface (18) that can, for example, stimulate bone growth, nerve regeneration, vascularization, and/or tissue repair. In some embodiments, the internal bulk (19) of the material substrate (8) is also modified. In such embodiments, the laser-scripted inductions (for example, the magnetic, ferroelectric, and piezoelectric features) extend into the internal bulk (19) of the material and their influence is propagated from the bulk (19) to the surface (8) where communication with the stem cells occurs.

In some embodiments, the laser genotype pulse scripts (6) are derived from the underlying chemical physics, solid-state dynamics, and photochemistry associated with the laser-material interactions. In some embodiments, the laser genotype pulse scripts (6) are spatially- and temporally-synchronized, and administered to prepare pre-determined phases, compositions, dispositions, and inductions in materials for regulating cell activity and defining cell phenotype.

In some embodiments, the laser genotype pulse scripts (6) result in a modified surface (18) having biomimetic architectures that are capable of retaining biological instructions through a variable bio-geometry that is perceived in surface and bulk (volume) response, and through inductive and conductive pathways resulting from phase disposition and composition. In some embodiments, one or more modified surfaces (18) includes micro-structural modifications, nano-topography alterations, and/or patterns with an appropriate repetition and/or design for enhancing a biological response. In some embodiments, the laser-induced modified surfaces (18) include charge distribution, electric field variation, standing voltaics, and/or capacitively-contained field charges to accentuate cell differentiation and tissue regeneration. In some embodiments, the laser-induced modified surfaces (18) include conductive, instructive, and inductive properties. In some embodiments, the laser-induced modified surfaces (18) are manifested as magneto-mechanical, electromechanical (ferroelectric, piezoelectric), and/or elementally enhanced inclusions that are configured to regulate cell chemistry and drive discrete phenotype expression.

In some embodiments, the method of controlling stem cell differentiation and gene expression is executed in vivo. In some embodiments, smart bioactive implants (interbody) and inner body devices are fabricated using laser genotype pulse scripts (6) to create modified surfaces (18) and/or internal bulk locations (19) locations comprising molecular tapestries having engineered inclusions and interconnected biological networks. In some embodiments, the laser-tailored modifications and inductions can be superimposed on the surface(s) of known material substrates (4), such as skeletal implant structures and related interbody devices. The material substrates (4) can be used for various applications including, without limitation, surgical repairs, orthopedic restoration, regenerative medicine, and pain mitigation therapies. In some embodiments, the material substrate (4) is used for, for example, bone fusion and vascularization in implant devices. In some embodiments, the material substrate (4) includes a passive structural system having physical and chemical properties intended to align with, for example, human bone, to enable mechanical integrity and biocompatibility for long-term acceptance in a skeletal structure. In some embodiments, the material substrate (4) is an implant. One of ordinary skill in the art would appreciate that known approaches or techniques are used to facilitate integration of a material substrate, such as the implant, into a human body.

In some embodiments, an implant can be designed to retain its structural and functional form to offer natural bone-like compliance and bio-compatible integration, and also to contain an exclusive set of laser-encoded genetic instructions to guide stem cell activity and define phenotype. In such embodiments, for example, the implant can include a plurality of laser-induced modified surfaces (18) for biological effect, the modifications including: specific surface features and textures to accentuate cell attachment and proliferation, improving tissue ingrowth and bone growth for implant stabilization and long-term integration; specific surface compositions, functionalization and reactivity to govern cell division and gene expression, promoting vascularization and blood flow for nutrient distribution; and specific electrical, magnetic, and mechanical inductions to stimulate cell response and define phenotype, providing nerve networks and neural channels for cell-cell communication and bio-feedback.

Figure 3A:
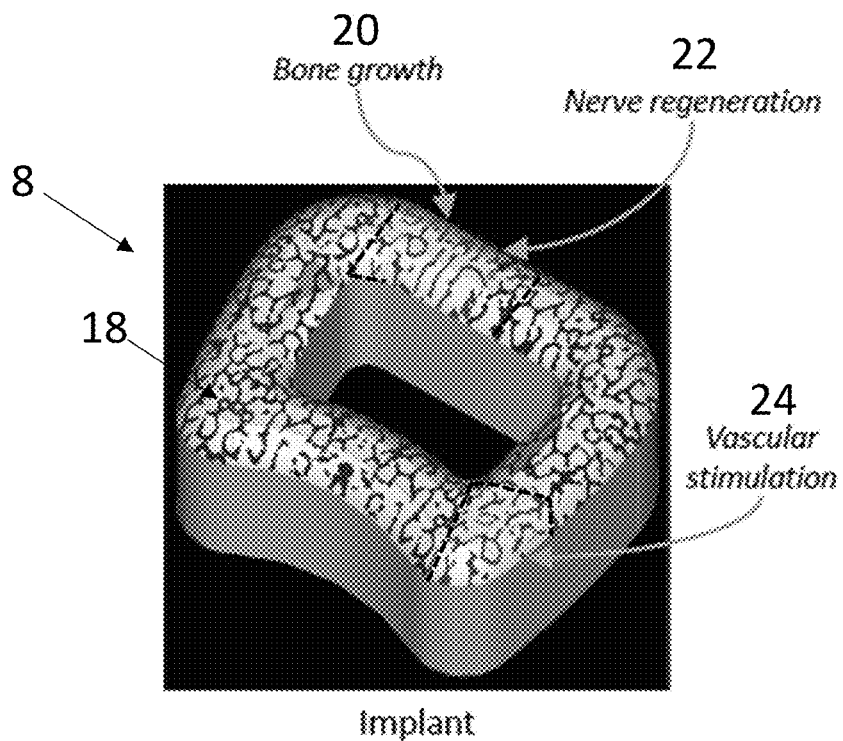
FIG. 3A is a perspective view of a material substrate having multi-functional bio-active instructions encoded thereon.
Figure 3B:
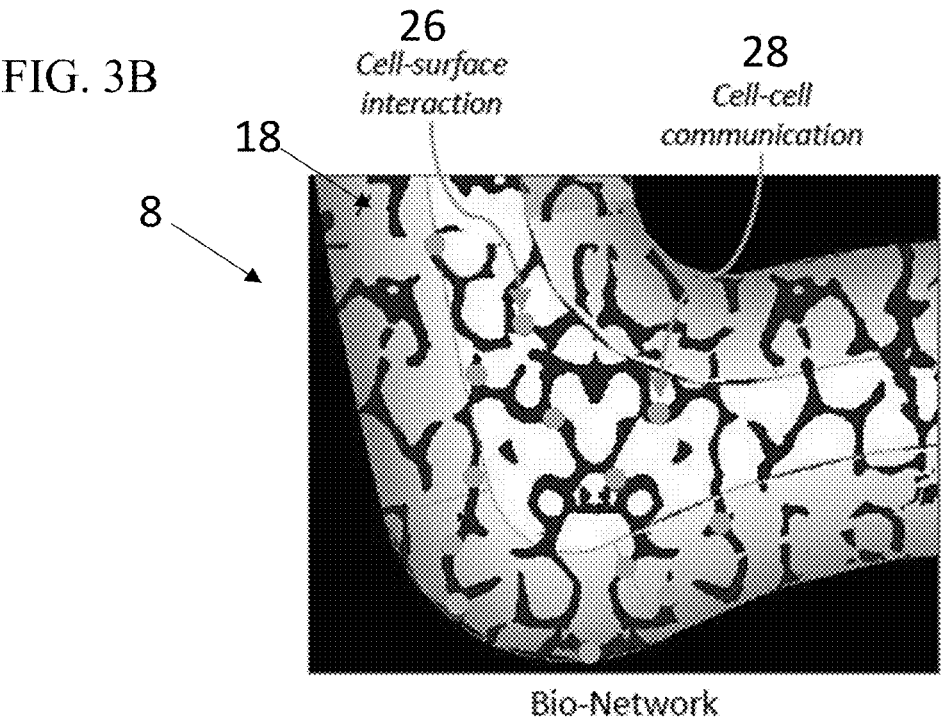
FIG. 3B is a partial view of a material substrate having multi-functional bio-active instructions encoded thereon, in accordance with some embodiments of the present disclosure.

As shown in FIG. 3A and FIG. 3B, for example, the modified material substrate (8), a spinal implant, has a modified surface (18) with laser-tailored molecular tapestries comprising engineered inclusions and interconnected biological networks. FIG. 3A shows a combination of modifications, including a portion designed to improve bone growth (20), a portion designed to improve nerve regeneration (22), and a portion designed to promote vascularization (24). FIG. 3B shows magnified area of the modified material surface (8) in FIG. 3A. In FIG. 3B, the modified surface (18) comprises additional interconnected biological networks, including a plurality of areas programed for cell-surface interaction (26) and an area for cell-cell communication (28). The pattern, texture, and morphology of the molecular tapestries superimposed and/or engraved on the modified surface (18) of the implant are integrated into a bionetwork comprising micro-structural modifications and nano-topography alterations. In some embodiments, the laser process physically modifies the surface and the interior bulk of the substrate, which can be manifested as various dispositions, phases, and inductions.

Figure 4A:
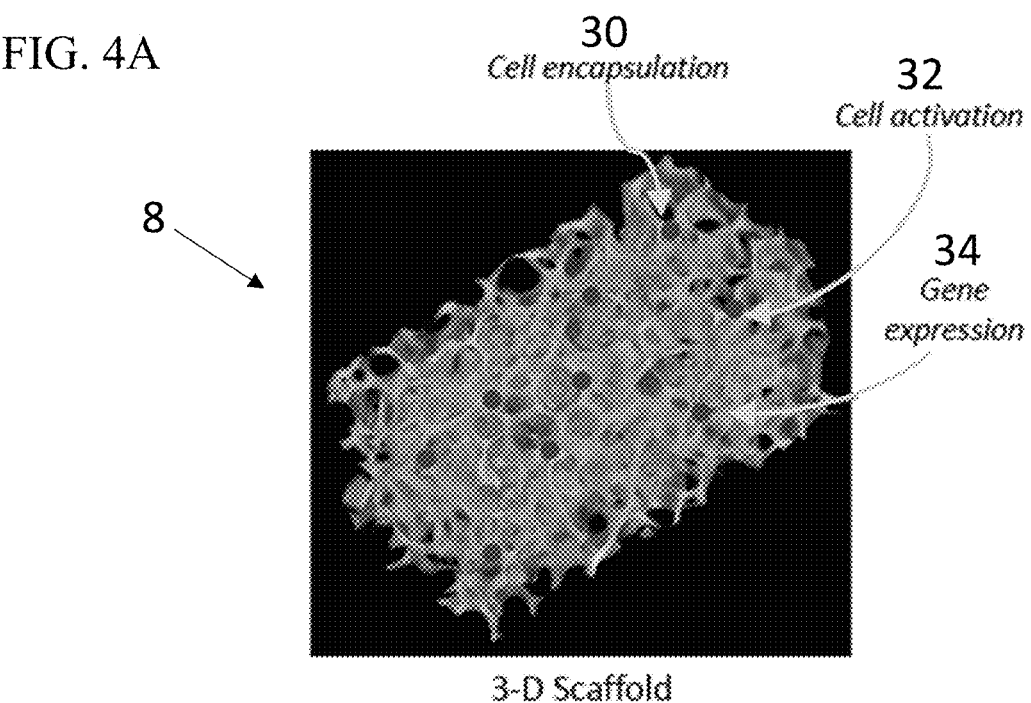
FIG. 4A a perspective view of a 3-D bio-instructive scaffold having multi-functional bio-active instructions encoded thereon.
Figure 4B:
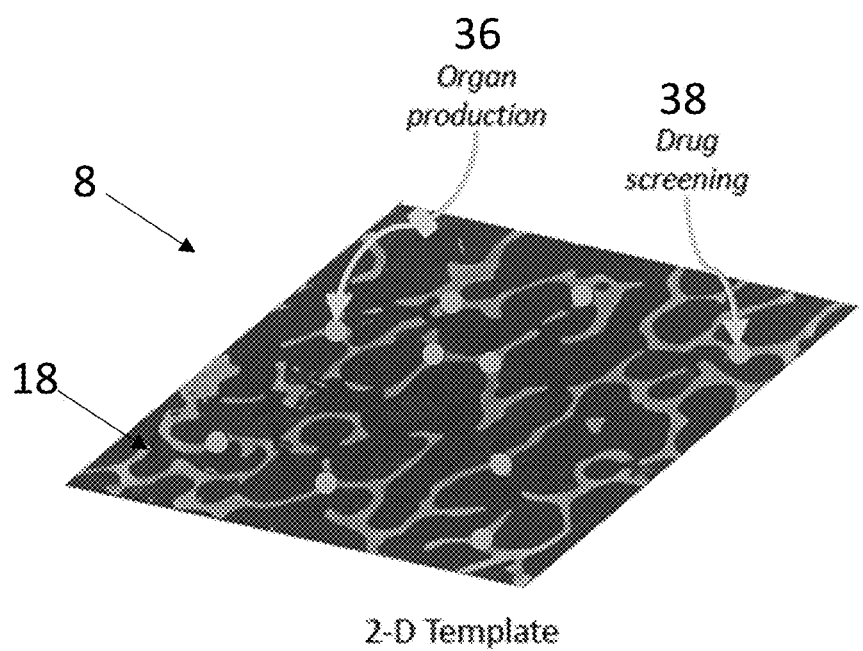
FIG. 4B is a perspective view of a 2-D template having multi-functional bio-active instructions encoded thereon, in accordance with some embodiments of the present disclosure.

In some embodiments, the method of controlling stem cell differentiation and gene expression is executed in vitro, presenting non-pharmacology options for regenerative medicine, tissue engineering, organ production, and drug screening. In some embodiments, in vitro applications include stem cell programming for drug screening and drug interaction investigation, as well as tissue and organ production. For in vitro applications, laser-scripted cell programming can be used to fabricate novel bioactive scaffolds and biomolecular templates. In FIGS. 4A and 4B, for example, a spot-by-spot laser tailoring process was implemented to create structural and material modifications comprising a variety of pre-programmed phases, inductions, and transductions that are configured to produce scaffolds and templates that retain high-level cooperative behavior in 2-D, 3-D, 4-D, 5-D, etc. By combining the appropriate scaffold structure and the modified material substrates (8) having the proper spatial distribution of material alterations, the resulting biomimetic architecture can provide an ECM-like environment for controlling cell activity and cell delivery and for defining cell phenotype and gene expression (cell lineage). In FIGS. 4A and 4B, the laser genotype pulse scripts (6) provided a plurality of modified areas configured, for example, for cell encapsulation (30), cell activation (32), gene expression (34), organ production (36), and drug screening (38).

Examples

Various embodiments will be further clarified by the following examples. The following examples are set forth below to illustrate the systems, methods, and results according to the disclosed subject matter. These examples are not intended to be inclusive of all embodiments of the subject matter disclosed herein, but rather to illustrate representative systems, methods, and results. These examples are not intended to exclude equivalents and variations of the present disclosure which are apparent to one skilled in the art.

Figure 5A:
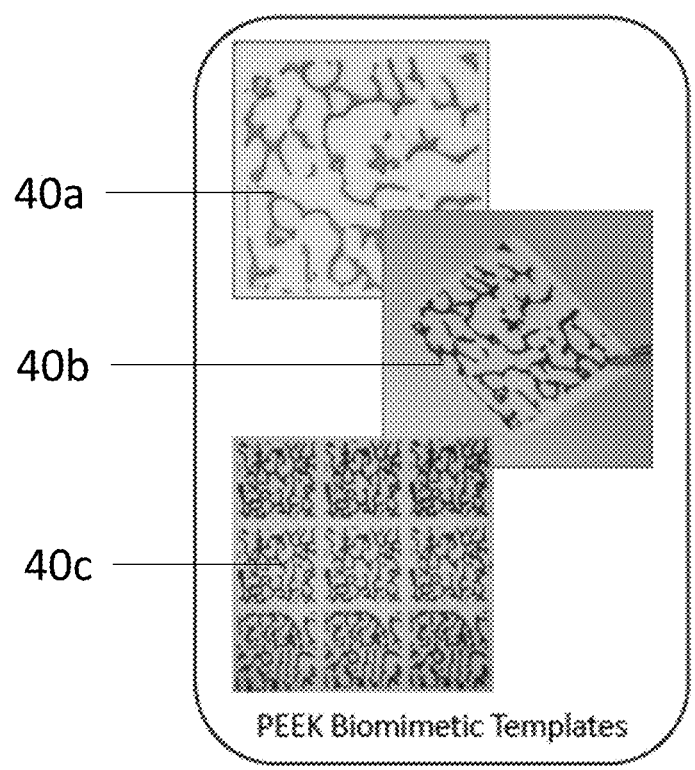
FIG. 5A shows biomimetic templates fabricated using laser-scripted genotype encoding.
Figure 5B:
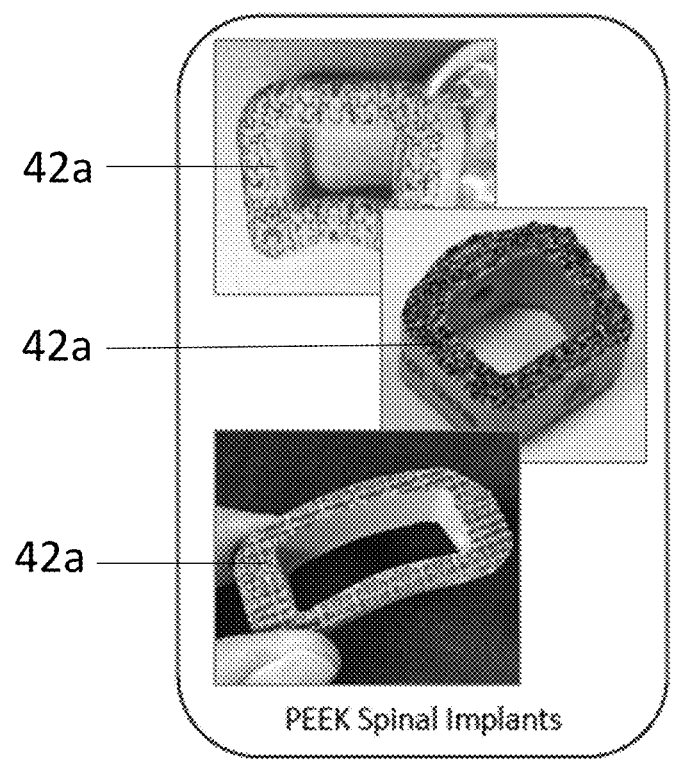
FIG. 5B shows biomimetic spinal implants fabricated using laser-scripted genotype encoding.
Figure 5C:
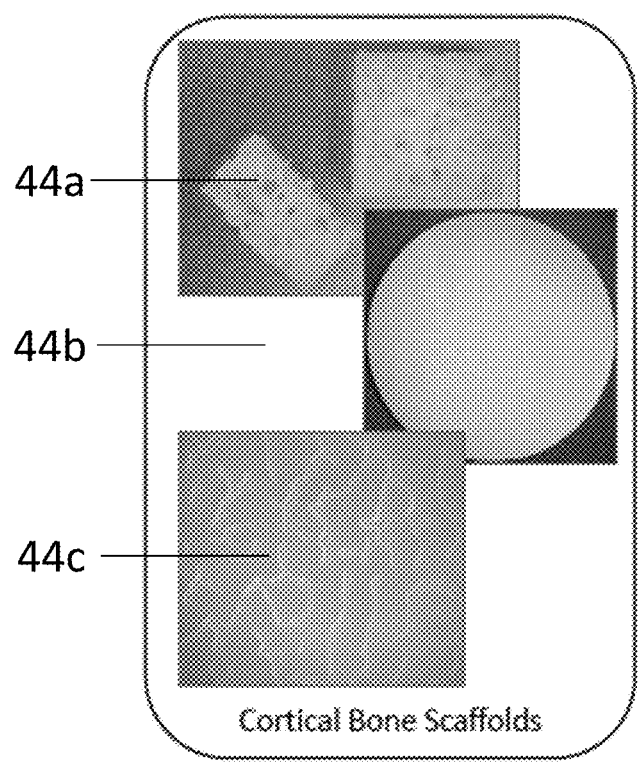
FIG. 5C shows biomimetic biomolecular scaffolds in human cadaver allografts fabricated using laser-scripted genotype encoding, in accordance with some embodiments of the present disclosure.

The ability to precisely govern cell activity and define phenotype is demonstrated through the laser-scripted genotype processing of some commonly employed biomaterials, such as biocompatible organic thermoplastics and authentic bone. Without limitation, these material systems are suitably represented herein with polyetheretherketone (PEEK), polyetherketoneketone (PEKK) and human allografts (cortical bone). An extensive variety of substrate forms and material types have been laser-tailored, endowing the material systems with genetic instructions and biological signatures that enable exquisite control of cell activity and cell fate. As shown in FIGS. 5A-5C, the laser-modified substrates include: biomimetic templates comprising 2-D and 3-D coupons, ultrathin films, and patterned arrays in PEEK (40a, 40b, 40c) (FIG. 5A); spinal implants corresponding to sheep cervical spacers and human cervical and lumbar interbody devices (42a, 42b, 42c) (FIG. 5B); and cortical bone scaffolds and bio-resonant architectures (44a, 44b, 44c) (FIG. 5C). These exemplar biomimetic structures have been successfully employed in a range of biomedical applications, including tissue ingrowth and bone fusion studies related to large animal trials and clinical evaluation, and cell culture studies related to organ production and stem cell therapies.

In some embodiments, the biomimetic character manifests as bio-geometric patterns that are superimposed with spatially-synchronized topography, surface textures, and physics-based inductions. For example, the laser-processed organic thermoplastics retain biomimetic patterning for cell corralling (aggregation) and cell alignment, micro- and nanoscale surface structuring for cell attachment and fixation, mechanical inductions for cell activation and cell proliferation, and electrical inductions for cell communication and gene expression. Additionally, the laser-tailored human allograft samples contained distinct piezoelectrically activated hydroxyapatite (HA) laminations that were preferentially extracted from the allograft matrix, forming sheets of variable HA content with the simultaneous reduction of the native collagen binder. The piezo-inductions are significant for their efficacy in controlling key biological processes, including cell-cell signaling, phenotype definition, cytoskeletal organization, and gap-junction communication.

Figure 6A:
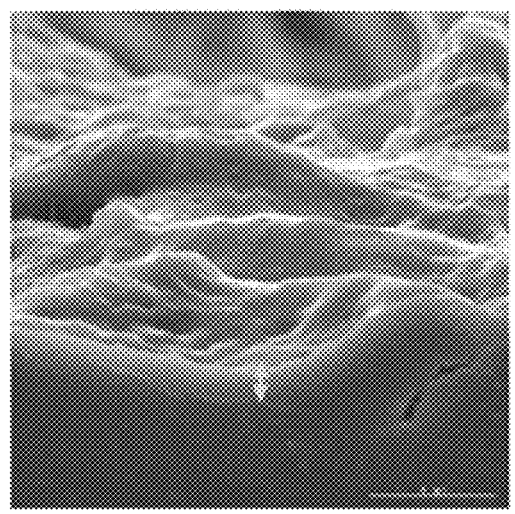
FIG. 6A is a scanning electron microscope (SEM) image of a non-patterned PEEK spinal implant (i.e., native PEEK)
Figure 6B:
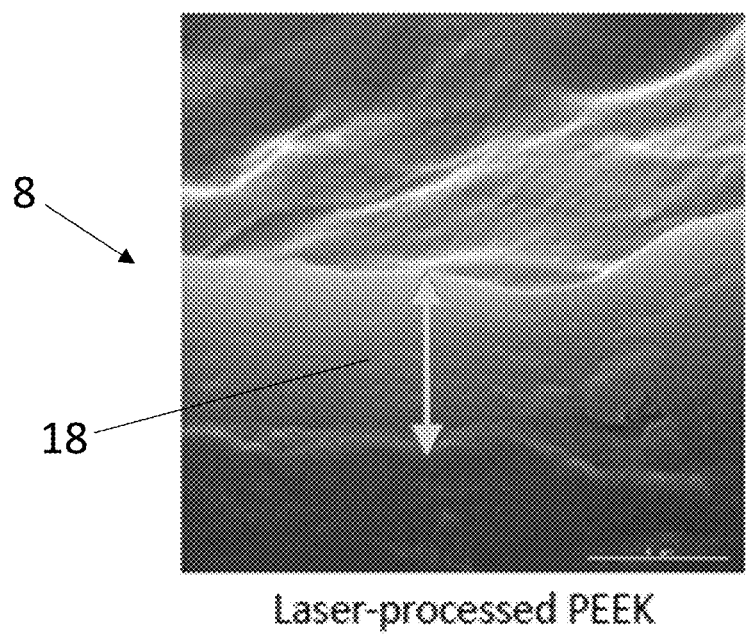
FIG. 6B is a SEM image of a laser-processed PEEK spinal implant.
Figure 6C:
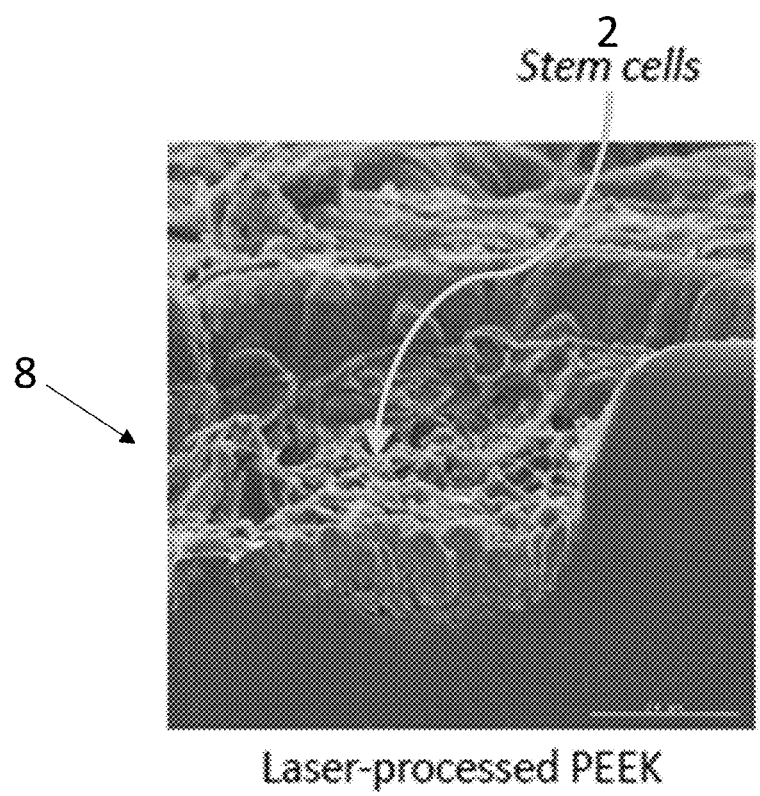
FIG. 6C is a SEM image showing the aggressive deposition and adhesion of marrow-isolated adult multilineage inducible (MIAMI) stem cells on a laser-patterned PEEK spinal implant, in accordance with some embodiments of the present disclosure.

As shown in FIGS. 6A-6C, the laser-scripted biomimetic processing of a PEEK implant device showcases the capability to control and accentuate the adhesion and interaction of stem cells. For comparison, FIG. 6A shows a scanning electron microscope (SEM) image of a non-patterned PEEK spinal implant (i.e., native PEEK). The bio-geometries were created using concatenated pulse sequences based on the laser-PEEK interaction physics and designed for overlapping multiple discrete material alterations. Both anisotropic and isotropic microstructures were fabricated in spatial resonance with the macro-pattern and micro-depth dimensions, ranging from coral-like architectures to well-ordered concentric laminations. These "frozen" microstructure extensions at the channel interface mimic lamellar bone formation, offering resemblance to cancellous bone architecture and mechanics (i.e., concentric laminations to offer plying support against tension and to strengthen early cell deposition). Phase alterations and electrical inductions (in situ electric field gradients) were also created within the otherwise insulating PEEK matrix, enabling the fabrication of connected electrical networks for current flow and cell regulation. FIG. 6B is a SEM image of a laser-processed PEEK spinal implant. The stem cells were observed to deposit preferentially on the biomimetically-patterned regions. FIG. 6C is a SEM image showing the aggressive deposition and adhesion of marrow-isolated adult multilineage inducible (MIAMI) stem cells on a laser-patterned PEEK spinal implant.

In vitro cell culture studies revealed that stem cells reacted to the bio-geometry and followed the architecture of the laser-tailored pattern. Site-specific stem cell matrix deposition on the laser-activated regions greatly exceeded that on the native substrate material, achieving enhanced deposition and tight adhesion without exuberant or indiscriminate proliferation. Similar improvements in cell attachment, fixation, and motility have been achieved through the laser-scripted processing of other biomedically relevant materials, including PEKK, allograft matrices and bone fillers, and titanium substrates.

Once attached with tight apposition to the laser-enhanced biomimetic surfaces, PCR (polymerase chain reaction) techniques were used to quantitatively examine stem cell differentiation and gene expression resulting from the laser-scripted processing conditions. Digests of laser biomimetic pulse scripts that elicit specific cell responses and express discrete cell lineages, targeting osteogenic (bone-forming) and neural (nerve-forming) genes, were obtained. For osteogenic differentiation, three key bone-related genetic markers exhibited pronounced and selective enhancement following the application of prescribed laser pulse sequences to human cortical bone, including Osterix (Osx), bone sialoprotein (BSP), and alkaline phosphatase (AlkP).

Figure 7:
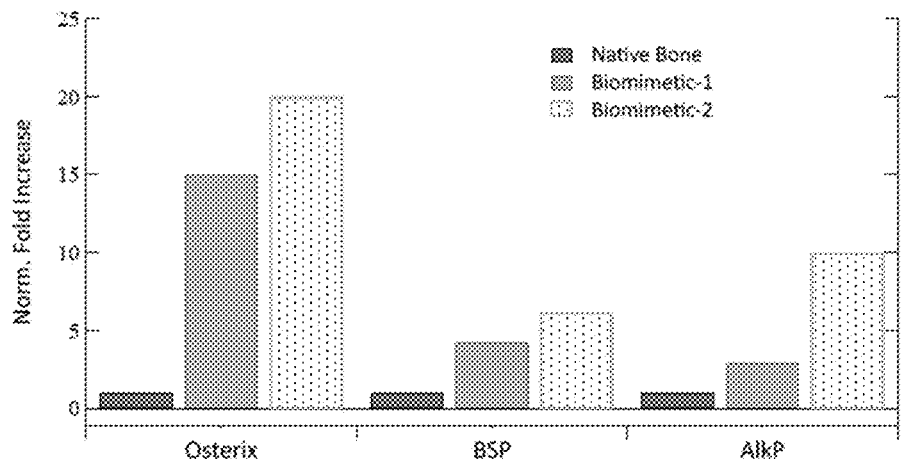
FIG. 7 is a graphical representation of the expression of osteogenic (bone-forming) differentiation markers Osterix, BSP, and AlkP in native and laser-tailored cortical bone samples (human allografts)

As shown in FIG. 7, the results corresponding to the administration of two representative laser genotype pulse scripts, denoted as Biomimetic-1 and Biomimetic-2, were significantly better than the result obtained in the native environment. Cortical bone samples that had undergone laser biomimetic processing showed between a 15- to 20-fold increase in Osterix compared with their native bone counterparts. Osterix is essential for osteoblast differentiation and for new bone formation in both growing and adult bones and is also recognized as having a critical role in the genetic programming of osteocytes. Osteoblasts are the cells that produce bone extracellular matrix and are responsible for its mineralization, while osteocytes are osteoblasts that have been incorporated into the bone matrix and are cells having extensive dendritic processes through which the cells communicate with other osteocytes and with osteoblasts. Through the development and administration of hundreds of laser genotype pulse scripts, it was discovered that the significant enhancements in Osterix expression and the preferential differentiation of stem cells into bone cells are principally governed by electrical inductions created within the substrate material. Laser genotype pulse scripting enabled the creation of patterned in situ electrical field gradients, resembling connected neural-type networks that can influence cell communication and proliferation, control cell differentiation and gene expression, and eliminate the need for traditional external electrical field stimulation.

Bone sialoprotein (BSP) and alkaline phosphatase (AlkP) levels were also significantly enhanced on the laser-processed cortical bone samples, showing normalized increases of between 3- to 5-fold compared with unprocessed cortical bone. BSP is a prime phenotypic marker for osteoblast differentiation and bone growth, stimulating initial hydroxyapatite formation and mediating cell-cell interactions and cell communications through integrin binding sites AlkP activity is important for the mineralization of bone and represents a useful biochemical marker of bone formation and pluripotency. The significant increases exhibited by these bone-forming genetic markers on the laser-tailored cortical bone samples were attained in the absence of osteogenic media or other chemical supplements. Each laser genotype pulse script (i.e., concatenated pulse sequence) triggered a distinct cell differentiation profile, thus offering an exclusive gene expression. These results demonstrate a new patient-specific option in stem cell therapeutics.

As shown in FIG. 8A, the results corresponding to the administration of two representative laser genotype pulse scripts, denoted as Biomimetic-3 and Biomimetic-4, were significantly better than the result obtained in the native environment. Specifically, for neural differentiation, the formation and activity of two nerve-specific genetic markers, Nestin and neurofilament-160 or NF160, were examined. These phenotypic markers are associated with the specification and differentiation steps in the neural-induction process, respectively. Nestin is a cytoskeletal protein widely employed as a marker of multipotent neural stem cells (NSCs) in developing and adult brains. Nestin is expressed in a variety of tissues and stem or progenitor cells, including skeletal muscle, heart and bone marrow. NF160 is a neurofilament protein that is important for neuronal structure and function. NF160 is particularly abundant in axons, where the protein is essential for axon radial growth and the transmission of electrical impulses along axons, i.e. velocity of nerve conduction.

Figure 8:
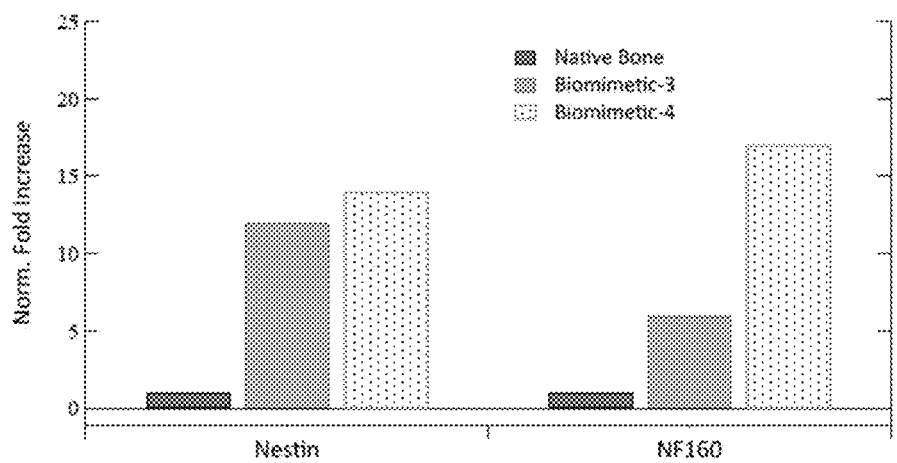
FIG. 8 is a graphical representation of the expression of neural (nerve-forming) differentiation markers Nestin and NF160 in native and laser-tailored cortical bone samples (human allografts)

As shown in FIG. 8, in the absence of laser-scripted biomimetic induction, essentially none of the mature neural markers were detected in the stem cells deposited on native cortical bone. The laser-tailored cortical bone samples, however, showed significant expression of both neural proteins: 12- to 14-fold normalized increases for Nestin and 7- to 17-fold normalized increases for NF160. Through the development and administration of hundreds of laser genotype pulse scripts, it was discovered that the significant enhancements in Nestin and NF160 expression and the preferential differentiation of stem cells into neural-type cells are principally governed by ferroelectric inductions created within the substrate material. Laser genotype pulse scripting enabled the preferential extraction of hydroxyapatite (HA) from the cortical bone (allograft matrix), forming domains of variable HA content along with a concomitant reduction of the native collagen binder. The laser biomimetic pulse sequencing was used specifically to control the conversion of the HA from the non-ferroelectric, non-piezoelectric monoclinic phase to the ferroelectrically-active and piezoelectrically-active hexagonal phase. The laser-induced modulations in phase states and the activation of ferroelectric and/or piezoelectric domains within the cortical bone represent the key drivers in stimulating the stem cells to differentiate into neural-type cells.

The results shown in FIG. 8 demonstrate the ability to program stem cells through energy-based transduction mechanisms, and control stem cell fate and gene expression with predefined laser pulse-script processing. For example, a preferential enhancement in neurofilament expression was achieved with two representative laser pulse scripts, denoted as Biomimetic-3 and Biomimetic-4. Both laser genotype pulse scripts induced nearly equivalent increases in Nestin levels, which corresponds to a reversible step in the neural-induction process. However, the Biomimetic-4 pulse script stimulated a significantly larger (3 times) fraction of NF160, which corresponds to an irreversible differentiation step in the neural-induction process. The laser-induced gene expression achieved within a subset of neural markers has an application in multi-functional devices comprising cooperative modalities, such as implants with distinct regions activated for bone growth, vascularization, and nerve formation.

Figure 9:
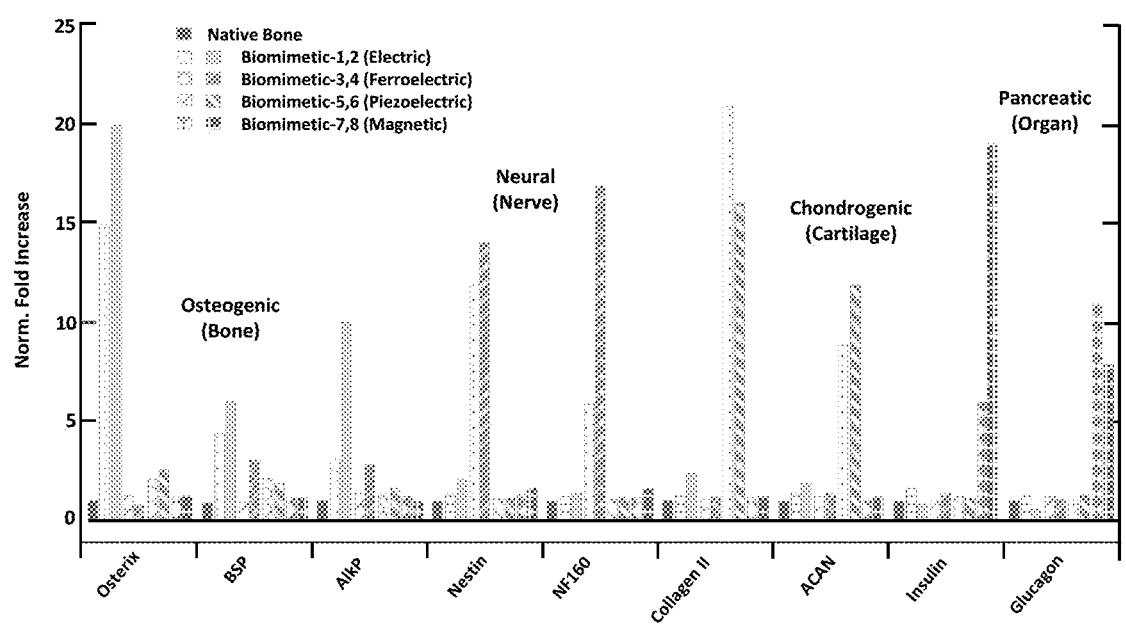
FIG. 9 is a graphical representation of the expression of various osteogenic, neural, chondrogenic, and pancreatic markers, in accordance with some embodiments of the present disclosure.

As shown in FIG. 9, the laser genotype pulse scripting process can be employed to achieve selective stem cell differentiation and programmable gene expression across many cell types, including bone cells, nerve cells, cartilage cells, and organ cells. The differentiation profiles shown in FIG. 9 correspond to a representative set of laser pulse scripts, which are denoted in pairs as Biomimetic-1,2; Biomimetic-3,4; Biomimetic-5,6; and Biomimetic-7,8. The principal laser-scripted alterations and inductions are included in parentheses for each pair of laser pulse scripts, and include such typical modifications as electrical inductions, ferroelectric inductions, piezoelectric inductions, and magnetic inductions.

The results shown in FIG. 9 demonstrate highly selective control of cell differentiation and cell type, achieving exclusive gene expression through the administration of specific laser pulse scripts. For example, cortical bone samples showed enhanced bone cell formation when processed with Biomimetic-1,2 along with the absence of appreciable differentiation to other cell types. When processed with Biomimetic-3,4, the cortical bone samples exhibited enhanced neural cell formation while differentiation to other cell types was not observed. Preferential differentiation of stem cells into cartilage cells was achieved through the application of Biomimetic-5,6 with a small fraction of conversion into bone cells as well. Further, enhanced differentiation of stem cells into organ cells was achieved on cortical bone samples that were processed using Biomimetic-7,8; while the expression of other cell types was intentionally avoided.

The results of FIG. 9 reveal that the programmed material modifications and inductions can be appropriately patterned and structured to create novel molecular tapestries and systems that mimic the cellular environment, combining all known requisite biological cues into a single interconnected, multi-functional biomimetic architecture. The biological architectures can be specially designed to include spatially-activated regions and inductions having the ability to stimulate pre-programmed multi-lineage character via autonomous and cooperative channels. For example, a laser-scripted molecular tapestry could be fabricated to strategically envelope a hip implant or similar device, creating a multi-functional biologically-active architecture that accentuates tissue ingrowth at one location, catalyzes bone secretion at another location, promotes nerve formation and vascularization at another location, and stimulates organ production at yet another location.

As disclosed herein, the laser-based approach couples patterned structural modifications and biological inductions to a material substrate, which enables the fabrication of multi-functional and intelligent material systems for controlling all forms of stem cell activity, including cell attachment and proliferation, cell differentiation, and gene expression. The laser processing methods described here provide unique options for stem cell instruction and gene expression through physics and energy-based transduction mechanisms, and avoid the complications and health and safety issues associated with traditional pharmacological approaches. The laser processing methods described here are applicable to regenerative medicine; restorative orthopedics; implant technology; tissue engineering; organ production; oncology; wound care; stem cell therapies; drug screening; pharmacological testing; cell separators; and dentistry.

Exemplary embodiments of the methods and devices are described above in detail. The systems and methods are not limited to the specific embodiments described herein, but rather, components of the systems and/or steps of the method may be utilized independently and separately from other components and/or steps described herein. For example, the system may also be used in combination with other systems and methods and is not limited to practice with only a system as described herein. Rather, the exemplary embodiment can be implemented and utilized in connection with many other systems.

Although specific features of various embodiments of the invention may be shown in some drawings and not in others, this is for convenience only. In accordance with the principles of the invention, any feature of a drawing may be referenced and/or claimed in combination with any feature of any other drawing.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method of creating a modified material substrate configured for stimulating and controlling stem cell differentiation, said method comprising:
   providing a material substrate configured for medical use, wherein the material substrate comprises at least one surface and interior bulk location available for modification, and
   treating the material substrate with a plurality of pulsed light beams to obtain a modified material substrate comprising at least one modified surface and at least one modified interior location, wherein the plurality of pulsed light beams extend into the interior bulk location to cause a laser-scripted induction modification including at least one of a magnetic feature, a ferroelectric feature, or a piezoelectric feature;
   wherein the at least one modified surface or interior location comprises a biomimetic architecture comprising surface and bulk features, properties, and textures configured to accelerate and control stem cell differentiation when the modified material substrate is contacted with stem cells, and wherein the laser-scripted induction modification exerts an influence during stem cell differentiation through the at least one modified surface of the material substrate.

2. The method according to claim 1, wherein the biomimetic architecture of the modified surface or interior location is based on a plurality of discrete laser genotype pulse scripts.

3. The method according to claim 1, wherein the plurality of light beams is derived from one or more laser genotype pulse scripts, wherein each laser genotype pulse script is configured to induce a biological result.

4. The method according to claim 3, wherein each laser genotype pulse script comprises a series of pulse sequences or individual pulses, each with their own characteristic wavelength, amplitude, pulse duration, polarization, coherence, or any combination thereof.

5. The method of claim 3, wherein the biological result comprises accentuating and controlling cell activity and cell function; cell attachment, cell motility, and cell proliferation; cell differentiation, phenotype and gene expression; improving tissue ingrowth and bone growth for implant stabilization and long-term integration; improving muscle regeneration and tendon growth; stimulating organ growth and regeneration; cell division and gene expression; promoting vascularization and blood flow for nutrient distribution; stimulating cell response; defining phenotype, or providing nerve- or neural-type networks and neural channels for cell-cell communication and bio-feedback.

6. The method according to claim 1, wherein the biomimetic architecture of the modified surface or interior location comprises micro-structural modifications, nano-topography alterations, textures, patterns, or any combination thereof, to enhance biologic response and cell efficacy.

7. The method of claim 1, wherein the biomimetic architecture of the modified surface or interior location comprises a charge distribution, electric field variation, standing voltaics, capacitively-contained field charge, compositional variations, phase alterations, or any combination thereof configured to accentuate and regulate cell differentiation and tissue regeneration.

8. The method according to claim 1, wherein the biomimetic architecture of the modified surface or interior location comprises conductive properties, instructive properties, inductive properties, transductive properties, or any combination thereof.

9. The method according to claim 1, wherein the biomimetic architecture of the modified surface or interior location comprises magneto-mechanical inclusions, ferroelectric inclusions, piezoelectric inclusions, pyroelectric inclusions, elementally enhanced inclusions, or any combination thereof, configured to regulate cell chemistry and drive discrete phenotype and gene expression.

10. The method according to claim 1, wherein the biomimetic architecture of the modified surface or interior location comprises an extracellular matrix (ECM)-like environment for controlling cell activity, cell transport, and cell delivery, or for defining cell phenotype and gene expression.

11. The method according to claim 1, wherein the plurality of pulsed light beams are based on a first laser pulse script generated by a computing device, wherein the computing device generates a plurality of command signals based on the laser pulse script, wherein a plurality of light beams are generated via an energy source, based on the plurality of command signals, and wherein the plurality of light beams are controlled based on the plurality of command signals to cause the surface or interior of the material substrate to be modified.

12. The method according to claim 1, wherein the material substrate is a biocompatible organic thermoplastic, a glass, a ceramic, a metal, a bone, an allograft, a semiconductor, a dielectric, or any combination thereof.

13. The method according to claim 1, wherein the material substrate comprises a substantially cylindrical substrate having a channel defining an internal surface therethrough.

14. The method according to claim 13, wherein the at least one surface comprises at least one of a top exterior surface or a bottom exterior surface of the substantially cylindrical substrate.

\* \* \* \* \*